US011455908B2

(12) United States Patent
Swartz (10) Patent No.: US 11,455,908 B2
(45) Date of Patent: Sep. 27, 2022

(54) SENSORY STIMULATION TOYS

(71) Applicant: Renee Swartz, Eugene, OR (US)

(72) Inventor: Renee Swartz, Eugene, OR (US)

( * ) Notice: Subject to any disclaimer, the term of this patent is extended or adjusted under 35 U.S.C. 154(b) by 449 days.

(21) Appl. No.: 16/718,176

(22) Filed: Dec. 17, 2019

(65) Prior Publication Data

US 2020/0193860 A1     Jun. 18, 2020

Related U.S. Application Data

(60) Provisional application No. 62/780,606, filed on Dec. 17, 2018.

(51) Int. Cl.
| | | |
|---|---|---|
| *A61M 21/02* | (2006.01) | |
| *G09B 19/00* | (2006.01) | |
| *A61M 21/00* | (2006.01) | |

(52) U.S. Cl.
CPC ............ *G09B 19/00* (2013.01); *A61M 21/02* (2013.01); *A61M 2021/0016* (2013.01); *A61M 2021/0022* (2013.01); *A61M 2021/0027* (2013.01); *A61M 2021/0044* (2013.01)

(58) Field of Classification Search
CPC .. A63B 23/16; A61H 2205/067; A61M 21/02; A61M 2021/0016; A61M 2021/0022; A61M 2021/0027; A61M 2021/0044
See application file for complete search history.

(56) References Cited

U.S. PATENT DOCUMENTS

| | | | | |
|---|---|---|---|---|
| 3,612,521 A * | 10/1971 | Wendeborn | ............ | A63B 23/16 D24/214 |
| 4,679,799 A * | 7/1987 | Coletti | ................... | A63B 65/00 473/505 |
| 4,828,249 A * | 5/1989 | Keating | ................. | A63B 23/16 482/121 |
| 5,062,625 A * | 11/1991 | Vonk | ................... | A63B 21/4019 482/48 |
| 5,556,186 A * | 9/1996 | Pilby | ....................... | F21V 11/02 362/342 |
| 6,179,751 B1 * | 1/2001 | Clears | ................ | A63B 21/4019 482/44 |
| 6,817,967 B1 * | 11/2004 | Ott | ..................... | A63B 21/4019 482/47 |
| 6,986,728 B2 * | 1/2006 | Kasun | ................ | A63B 21/4025 482/44 |

(Continued)

*Primary Examiner* — Kaylee R Wilson
(74) *Attorney, Agent, or Firm* — Miller IP Law LLC (57) ABSTRACT

A method, system, apparatus, and/or device to provide a therapy toy to stimulate one or more senses of a person. The therapy toy may include: a perimeter sub-structure including a first side strip, a top strip, a second side strip, and a bottom strip; and a center grid sub-structure including a first center strip and a second center strip. The first center strip and the second center strip may extend from a first side of the perimeter sub-structure to a second side of the perimeter sub-structure. The first center strip and the second center strip may be connected at multiple points to form the holes. The fabric grid structure comprises a material having a pliability or a compressibility sufficient to allow the fabric grid structure to be collapsed or deformed by a hand of the person. The person may use the therapy toy therapeutically.

10 Claims, 8 Drawing Sheets

(56) References Cited

U.S. PATENT DOCUMENTS

| | | | | |
|---|---|---|---|---|
| 7,121,983 B1* | 10/2006 | Trent | ................... | A63B 23/14 |
| | | | | 482/121 |
| 7,678,440 B1* | 3/2010 | McKnight | ................ | B32B 3/26 |
| | | | | 148/563 |
| 2016/0291447 A1* | 10/2016 | Branham | ............... | G03B 15/06 |

* cited by examiner

SENSORY STIMULATION TOYS

BACKGROUND

Our bodies take in information through sensory systems, such as auditory information, olfactory information, gustatory information, tactile information, vestibular information, and so forth. Sensory integration is the process that a central nervous system goes through when it takes in the sensory information from a body's senses, processes that information, and then responds accordingly. When an individual's central nervous system has difficulty processing any of this sensory information, the body's responses are atypical and can be observed in motor, language, or behavioral skill difficulties. For example, an individual with autism may process sensory information differently and have atypical responses to sensory information. Individuals with difficulties processing sensory information may use apparatuses such as toys, playthings, trinkets, and so forth to process sensory information. The apparatuses may aid individuals with difficulties processing sensory information because when one or more of the senses of the individual are engaged, the individual may be able to mentally focus and process other senses.

BRIEF DESCRIPTION OF THE DRAWINGS

The present description will be understood more fully from the detailed description given below and from the accompanying drawings of various embodiments of the present embodiment, which is not to be taken to limit the present embodiment to the specific embodiments but are for explanation and understanding.

DETAILED DESCRIPTION

The disclosed sensory stimulation toys will become better understood through review of the following detailed description in conjunction with the figures. The detailed description and figures provide merely examples of the various inventions described herein. Those skilled in the art will understand that the disclosed examples may be varied, modified, and altered without departing from the scope of the inventions described herein. Many variations are contemplated for different applications and design considerations; however, for the sake of brevity, each and every contemplated variation is not individually described in the following detailed description.

Throughout the following detailed description, a variety of sensory stimulation toy examples are provided. Related features in the examples may be identical, similar, or dissimilar in different examples. For the sake of brevity, related features will not be redundantly explained in each example. Instead, the use of related feature names will cue the reader that the feature with a related feature name may be similar to the related feature in an example explained previously. Features specific to a given example will be described in that particular example. The reader should understand that a given feature need not be the same or similar to the specific portrayal of a related feature in any given figure or example.

Sensory simulation apparatuses, such as sensory stimulation toys, provide particular sensory inputs that individuals with autism and/or difficulty processing sensory information may desire or help the individuals to mentally focus. For example, some visual or tactile sensory stimulation toys capture the individual's attention. Other sensory stimulation toys may be used to reinforce desired behaviors for the individual. Other sensory stimulation toys may enable the user to fidget with the toys to improve concentration and focus by engaging one or more senses, such as tactile senses with the individual's hands so the individual may listen and be attentive.

Conventional sensory simulation toys are limited in their ability to engage different senses. Additionally, conventional sensory simulation toys may lack multiple applications or uses. Implementations of the disclosure address the above-mentioned deficiencies and other deficiencies by providing a method, system, device, and/or apparatus to stimulate one or more senses of a user. The method, system, device, or apparatus may include a fabric toy with a grid having one or more holes. In one embodiment, the one or more holes may be configured to receive one or more fingers of a user. In another embodiment, the fabric toy may be a plush toy that is flexible or bendable to be configured into different variations. For example, the sensory simulation toy may be flexed or bent to have different shapes and show different colors.

Figure 1:
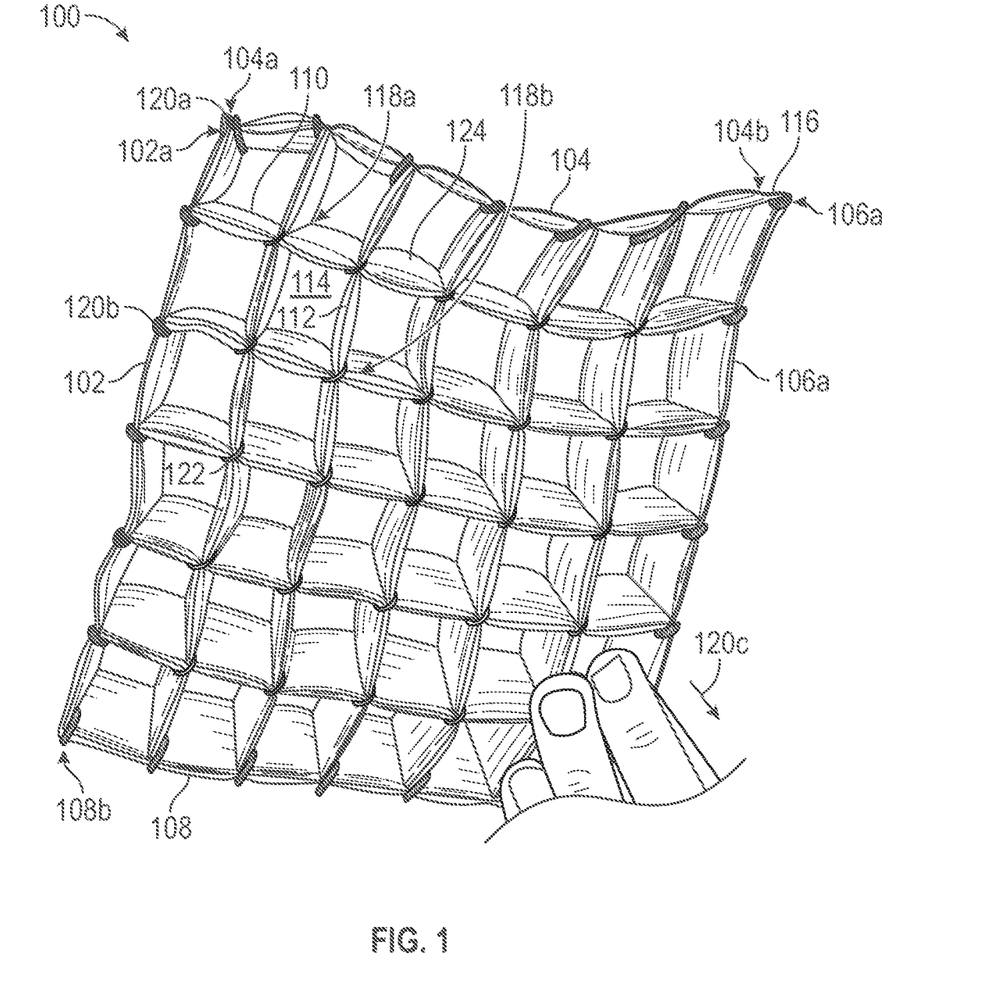
FIG. 1 illustrates a sensory stimulation toy, according to an embodiment.

FIG. 1 illustrates a sensory stimulation toy 100, according to an embodiment. The sensory stimulation toy 100 may be made of multiple strips of fabric. The multiple strips of fabric may be attached together to form a grid that a user may insert one or more fingers into holes 114 of the grid. Accordingly, the sensory stimulation toy 100 may include and/or be formed as a fabric grid structure. The grid may include a first side strip 102, a top strip 104, a second side strip 106, a bottom strip 108, a first center strip 110, and a second center strip 112. The first center strip 110 and the second center strip 112 may form the hole 114. The grid may include a plurality of the holes 114 formed by a plurality of center strips.

In one embodiment, to form a perimeter of the grid: a first end 102a of the first side strip 102 may be attached to a first end 104a of the top strip 104; a second end 104b of the top strip 104 may be attached to a first end 106a of the second side strip 106; a second end of the second side strip 106 may be attached to a first end of the bottom strip 108 (not visible in the FIG., but similar to the other strip ends described herein); and a second end 108b of the bottom strip 108 may be attached to a second end 102b of the first side strip 102. In another embodiment, the perimeter of the grid may be formed of a single strip. The first side strip 102 may be formed of a first segment of the single strip. The top strip 104 may be formed of a second segment of the single strip.

The second side strip 106 may be formed of a third segment of the single strip. The bottom strip 108 may be formed of a fourth segment of the single strip. The single strip may have a first end and a second end that are joined together, enclosing the grid. The first end and the second end may be joined at a corner 116 or in the first segment, the second segment, the third segment, or the fourth segment.

In one embodiment, the corner 116 may be formed by stitching together the second end 104b of the top strip 104 and the first end 106a of the second side strip 106. Other corners of the grid may be similarly formed: corner stitching may attach the first side strip 102 to the top strip 104; corner stitching may attach the second side strip 106 to the bottom strip 108; and/or corner stitching may attach the bottom strip 108 to the first side strip 102. The strips may be stitched together using, for example, a straight stitch, a running stitch, a zig-zag stitch, a slip stitch, a whipstitch, and so forth. In another embodiment, the corner 116 may be formed by folding the single strip into two sides and stitching the two sides together adjacent to the fold. The corner stitching may gather a relatively small segment (ranging, for example, from one millimeter to five millimeters in length) of the first side strip 102, the top strip 104, the second side strip 106, or the bottom strip 108 to form a corner such as the corner 116 in the respective strip.

In another embodiment, the corner 116 may be formed by a stitch that creates a crease in the single strip. The single strip may have a length and a width, where the length of the single strip is longer than the width of the single strip. The single strip may include stitching extending the width of the single strip. The stitching may form a crease in the single strip at which the single strip bends, thereby forming the corner 116. An angle of the corner 116 may be determined by a length of a center strip nearest the stitching (of the center strips) and/or where on the single strip the nearest center strip is attached to the single strip. The angle of the corner 116 may further be determined similarly by attachment of other center strips to the single strip and/or the nearest center strip.

To form the interior grid of the sensory stimulation toy 100, the first center strip 110 may extend from a first side of the perimeter to a second side of the perimeter and a second center strip 112 may extend from the first side of the perimeter to the second side of the perimeter. In one embodiment, the first center strip 110 and/or the second center strip 112 may extend across the grid diagonally. The first center strip 110 may be stitched to the first side strip 102 and the bottom strip 108, and the second center strip 112 may be stitched to the top strip 103 and the second side strip 106. The stitching may include a zigzag stitch, for example. The first center strip 110 and the second center strip 112 may be connected at multiple points along the first center strip 110 and the second center strip 112. For example, the first center strip 110 and the second center strip 112 may be connected at a first point 118a and a second point 118b, and may thereby form the hole 114 between the first center strip 110 and the second center strip 112. The first center strip 110 and the second center strip 112 may be connected by a straight stitch or a running stitch, and so forth.

In an embodiment, the hole 114 may be formed by stitching that pulls the strips defining the grid away from each other. For example, the grid may include a first attachment point 120a where the first side strip 102 and the top strip 104 attach to each other (i.e. at the first end 102a of the first side strip 102 and at the first end 104a of the top strip 104). The grid may include a second attachment point 120b where the first center strip 110 and the first side strip 102 attach to each other. The grid may include the first point 118a where the first center strip 110 attaches to the second center strip 112. A length of a first segment between the first attachment point 120a and the second attachment point 120b may be approximately equal to a length of a second segment between the second attachment point 120b and the first point 118a. The first segment may be adjacent and/or perpendicular to the second segment.

The grid may include a plurality of strips extending diagonally across the grid. For example, a third center strip 122 may extend across the grid structure from the first side strip 102 to the bottom strip 108 adjacent to the first center strip 110. A fourth center strip 124 may extend diagonally across the grid from the top strip 104 to the second side strip 106 adjacent to the second center strip 112. The third center strip 122 and the first center strip 110 may be connected at multiple points along the third center strip 122 and the first center strip 110. The multiple points along the third center strip 122 and the first center strip 110 may alternate along the first center strip 110 with the multiple points along the first center strip 110 and the second center strip 112. Accordingly, the third center strip 122 may pull the first center strip 110 away from the second center strip 112 at the multiple points along the third center strip 122 and the first center strip 110. Similarly, the fourth center strip 124 and the second center strip 112 may be connected at multiple points along the fourth center strip 124 and the second center strip 112. The multiple points along the fourth center strip 124 and the second center strip 112 may alternate along the second center strip 112 with the multiple points along the first center strip 110 and the second center strip 112. Accordingly, the fourth center strip 124 may pull the second center strip 112 away from the first center strip 110 at the multiple points along the fourth center strip 124 and the second center strip 112.

The center strips of the grid may include a variety of features for sensory stimulation, including visual, tactile, and audible sensory stimulation. In an embodiment, the first center strip 110 may include a first color pattern, the second center strip 112 may include a second color pattern, the third center strip 122 may include a third color pattern, and the fourth center strip 124 may include a fourth color pattern. The color pattern may include a set of shapes, designs, and/or colors of a strip forming the grid. The color patterns of the strips may alternate across the grid such that a particular color pattern may zigzag along a first diagonal of the grid and repeat along a second diagonal of the grid. A zigzag may refer to the center strips having segments of alternating direction, such as right-oriented alternating with left-oriented.

In another embodiment, the center strips may include alternating and/or varying fabric types. For example, the first center strip 110 may be formed of a first fabric type and the second center strip 112 may be formed of a second fabric type. The second fabric type may have a different texture than the first fabric type. Fabric types of the center strips may include a woven fabric, a knitted fabric, and/or a specialty fabric such as felt. Varying fabric types of the center strips may vary a tactile stimulation generated by touching the center strips. In one embodiment, the fabric may feel smooth. In another embodiment, the fabric may feel rough. In another embodiment, the fabric may have ribs and/or ridges. In various other embodiments, the fabric may feel silky, fluffy, scratchy, clingy, or slippery, and so forth. Varying fabric types of the center strips may vary an audio stimulation, as running skin across different types of fabric may create different sounds.

The hole 114 may be sized to receive a finger of a user, such as an individual using the fabric grid for therapy. In one example, the hole 114 may be a square shape. In this example, the area of the square may range between 35 millimeters (mm) and 75 mm in width and between 35 mm and 75 mm in height. In another example, the hole 114 may be circle shaped or oval shaped with a diameter between 35 mm and 75 mm. The area or diameter of the hole 114 may vary based on a size of the user's fingers. For example, when the user is a child, the area or the diameter of the hole 114 may be smaller than when the user is an adult. The number of center strips and the number of holes formed between the center strips may vary and is not intended to be limiting. In one example, the first center strip 110 and the second center strip 112 may be attached at multiple points to form multiple holes to receive multiple fingers of a user. In another example, the sensory stimulation toy 100 may include multiple center strips connected to each other to form a grid or lattice of holes to provide multiple holes for each of the fingers of the user. For example, the grid or lattice of the sensory stimulation toy 100 may be a square shape or diamond shape with multiple holes, such as 36 holes in a 6×6 grid as shown in FIG. 1. In another example, the grid or lattice of the sensory stimulation toy 100 may be oval shaped, circle shaped, triangle shaped, rectangle shaped, pentagon shaped, trapezoid shaped, octagon shaped, and so forth. In another example, the center strips of the grid may be connected to form a zigzag grid or a crisscross grid.

In another embodiment, the first side strip 102, the top strip 104, the second side strip 106, the bottom strip 108, the first center strip 110, and/or the second center strip 112 may be fabric material with foam fused to the inside of the fabric material. For example, the first side strip 102 may include folded fabric with foam fused with an interior cavity between the fold and then the edges of the fold may be sewn together to encapsulate the foam. The top strip 104, the second side strip 106, the bottom strip 108, the first center strip 110, and/or the second center strip 112 may similarly be infused with the foam. In one example, when the strips 102-112 are infused with foam, the strips 102-140b may provide a padding or cushion for the user when the user grabs the perimeter of the sensory stimulation toy 100 and/or inserts one or more of their fingers into the grid of the sensory stimulation toy 100. In another example, when the strips 102-112 are infused with foam, the strips 102-112 may provide a padding or cushion to provide a tactile feel to the user to stimulate tactile senses of the user. The height and/or thickness of the strips 102-112 may vary and is not intended to be limiting. For example, for a user with longer fingers, the height of the strips 102-112 may be taller than a user with shorter fingers.

In another embodiment, one or more of the strips 102-112 may be different colors or patterns of colors. For example, each of the strips 102-112 may be a different color so that when the user plays with the sensory stimulation toy 100, the sensory stimulation toy 100 may stimulate the visual senses of the user with the different color or patterns of colors. In another example, the grid may be a symmetric grid to provide symmetric colors and designs. In another embodiment, one or more of the strips 102-112 may be infused with fragrant material, such as essential oils. As the individual plays with the sensory stimulation toy 100, one or more fragrances may permeate from the strips 102-112 to stimulate the olfactory senses of the user. In one example, different strips 102-112 may be impregnated with different fragrances such that when the user smells different strips 102-112, the user may sense different smells.

Figure 2:
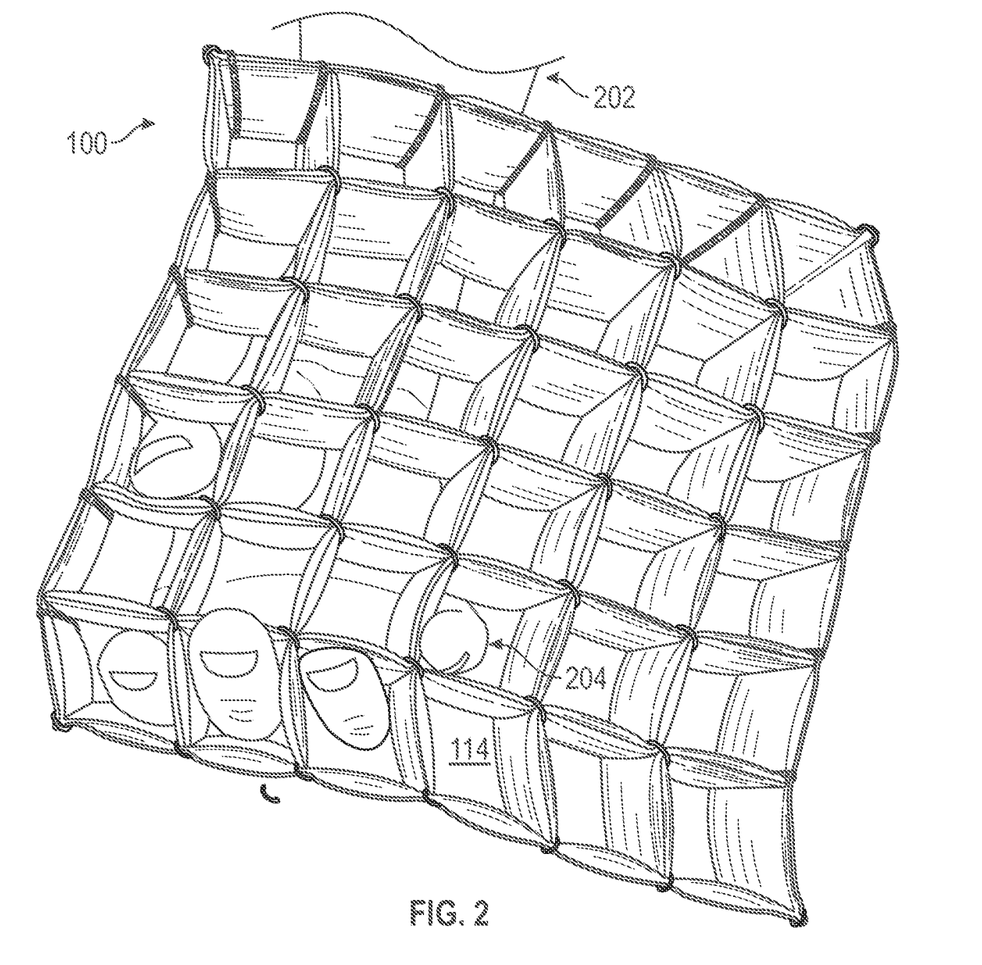
FIG. 2 illustrates a front view of a sensory stimulation toy with fingers of a user being inserted into multiple holes of the sensory stimulation toy, according to an embodiment.

FIG. 2 illustrates a front view of the sensory stimulation toy 100 with fingers 202 of a user 204 being inserted into multiple holes 114 of the sensory stimulation toy 100, according to an embodiment. Some of the features in FIG. 2 are the same as or similar to some of the features in FIG. 1 as noted by same and/or similar reference characters, unless expressly described otherwise. As discussed above, the user 204 may insert their fingers 202 into the holes 114 of the sensory stimulation toy 100 in order to play with and/or manipulate the sensory stimulation toy 100. The holes 114 may be large enough to accommodate a variety of finger sizes of a variety of users 204. The holes 114 may be small enough that the user's fingers 202 touch the fabric of the grid as the fingers 202 are inserted into the holes 114 at various angles. The holes 114 may be small enough that the user 204 may insert multiple fingers 202 into neighboring holes 114, such as to manipulate a shape of the sensory stimulation toy 100.

The user 204 may include an individual playing with the sensory stimulation toy 100. For example, the sensory stimulation toy 100 may be used by the individual as a fidget toy. The individual may use the sensory stimulation toy 100 to keep the individual's fingers and/or hands busy. The user 204 may include an individual with an attention disorder and/or disability such as an autism spectrum disorder, attention deficit disorder, attention deficit hyperactivity disorder, and so forth. The variety of visual, tactile, olfactory and/or auditory stimuli of the sensory stimulation toy 100 may help the user 204 focus on a task by occupying senses that might otherwise be overwhelmed by other, uncontrolled stimuli.

Figure 3A:
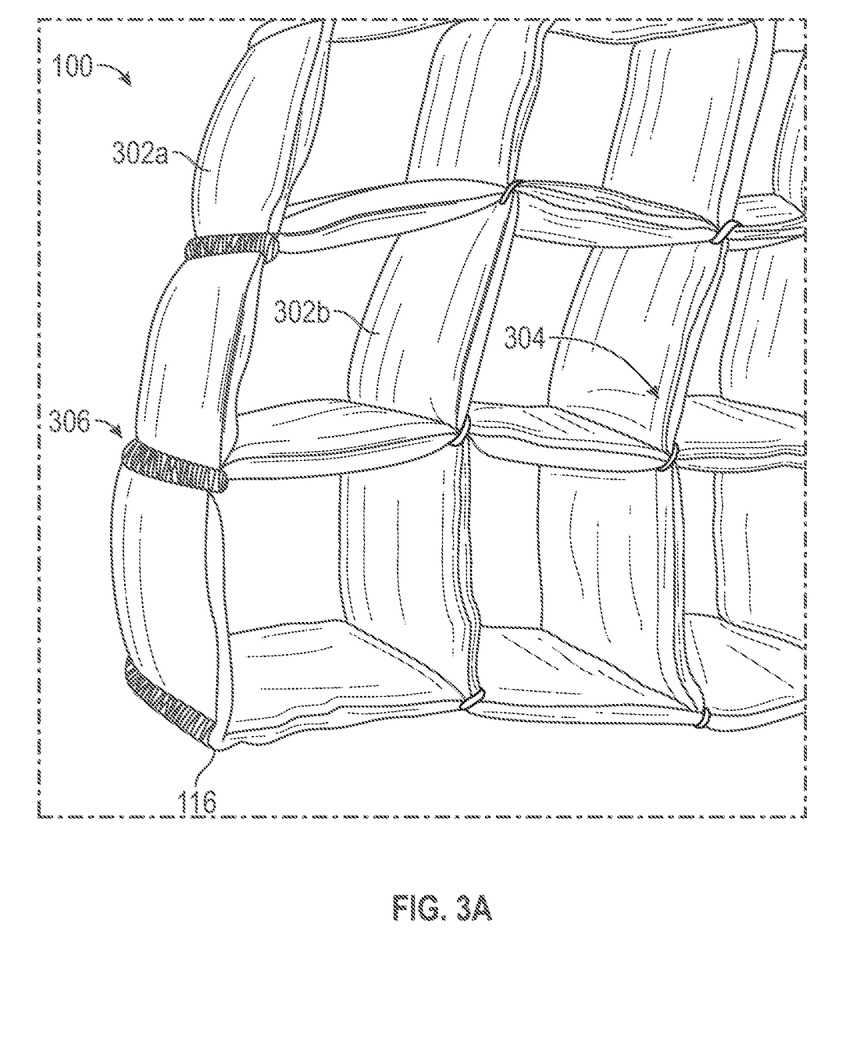
FIG. 3A illustrates a zoomed in front view of a sensory stimulation toy to show stitching of the sensory stimulation toy, according to an embodiment.

FIG. 3A illustrates a zoomed in front view of the sensory stimulation toy 100 to show stitching of the sensory stimulation toy 100, according to an embodiment. Some of the features in FIG. 3A are the same as or similar to some of the features in FIGS. 1-2 as noted by same and/or similar reference characters, unless expressly described otherwise. In various embodiments, the sensory stimulation toy 100 includes strips of fabric stitched together, such as a side strip 302a and a center strip 302b. The side strip 302a and/or the center strip 302b may be formed of a piece of fabric stitched together by a straight stitch 304. The straight stitch 304 may be visible or invisible. In embodiments where the straight stitch 304 is visible, edges of the piece of fabric may be folded inwards to protect the edges. The center strip 302b may be attached to the side strip 302a by zigzag stitching 306. The zigzag stitching 306 may also be used to form the corner 116 as described regarding FIG. 1.

Figure 3B:
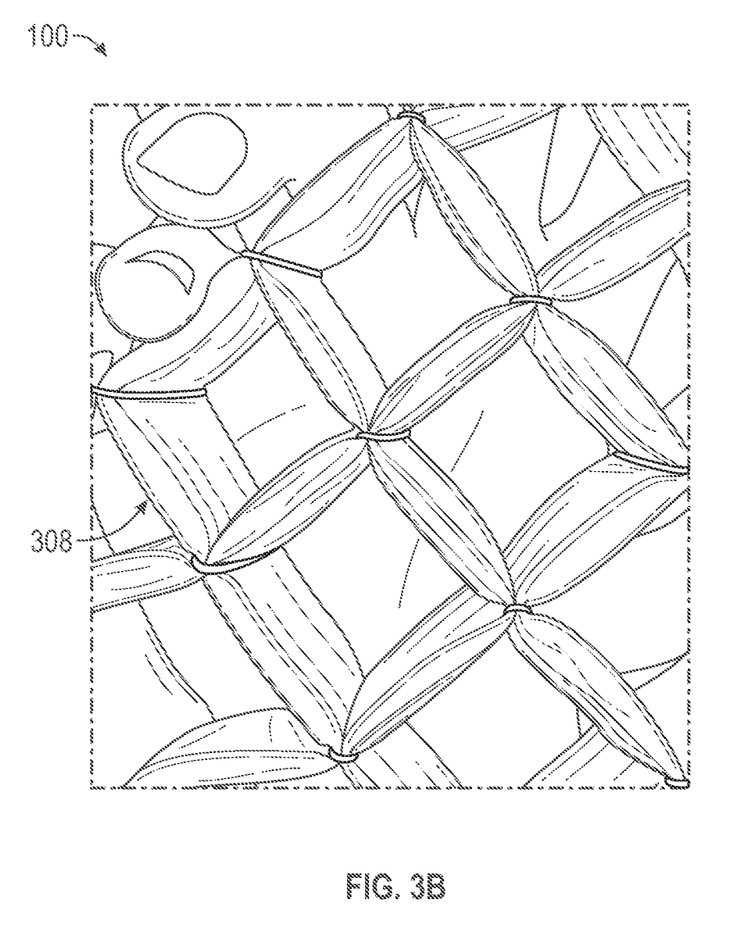
FIG. 3B illustrates a zoomed in back view of the sensory stimulation toy, according to an embodiment.

FIG. 3B illustrates a zoomed in back view of the sensory stimulation toy 100, according to an embodiment. Some of the features in FIG. 3B are the same as or similar to some of the features in FIGS. 1-3A as noted by same and/or similar reference characters, unless expressly described otherwise. As described above, the side strip 302a and/or the center strip 302b may be formed of a piece of fabric. The piece of fabric may be folded together so that one side of the fabric (such as is shown in FIG. 3A) includes edges of the fabric stitched together and the opposite side (such as is shown in FIG. 3B) includes a continuous rounded edge 308.

Figure 4:
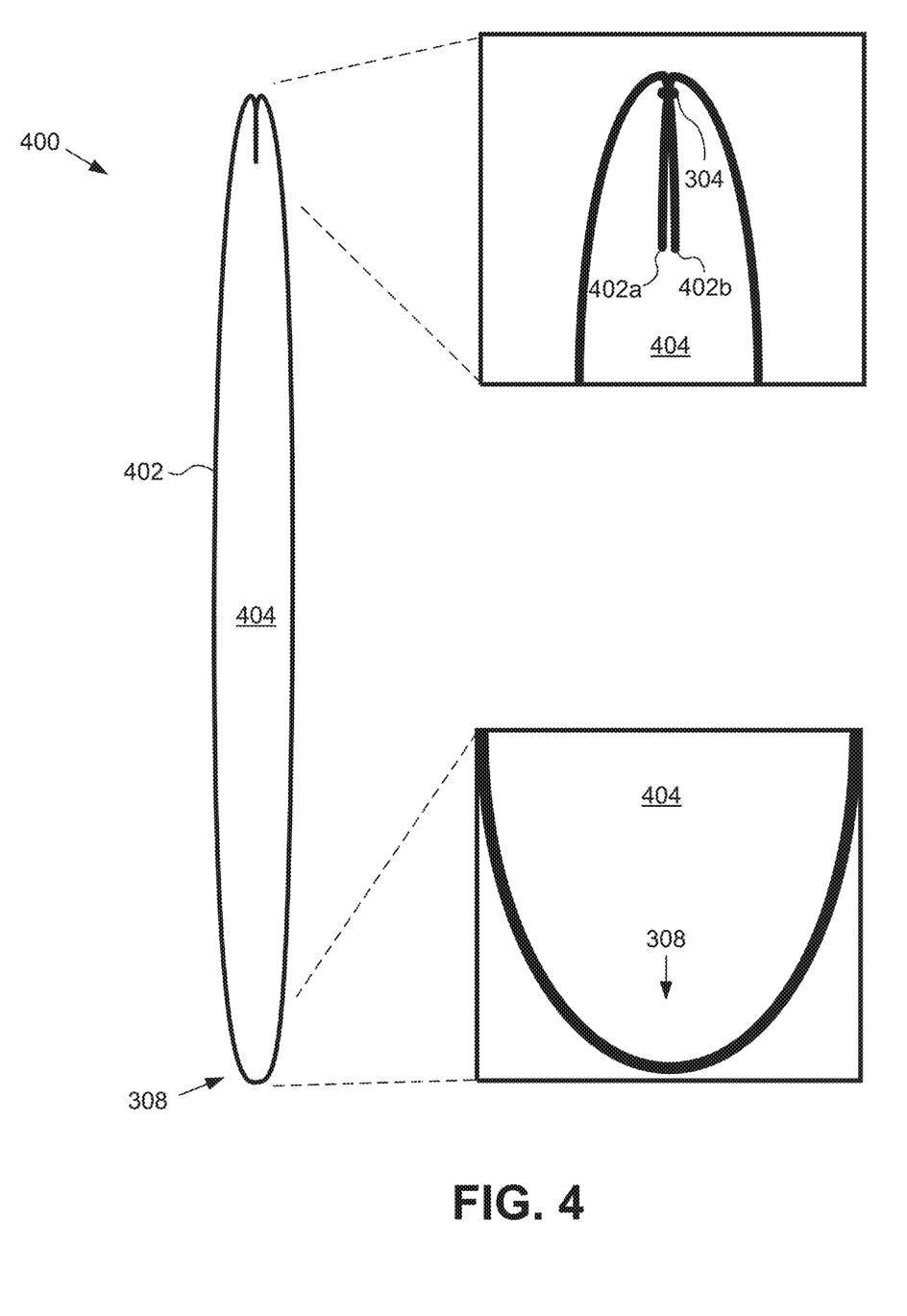
FIG. 4 illustrates a schematic and callouts of a side cross-section of a fabric strip used to form a sensory stimulation toy, according to an embodiment.

FIG. 4 illustrates a schematic and callouts of a side cross-section of a fabric strip 400 used to form the sensory stimulation toy 100, according to an embodiment. Some of the features in FIG. 4 are the same as or similar to some of the features in FIGS. 1-3B as noted by same and/or similar reference characters, unless expressly described otherwise. The fabric strip 400 may include a single piece of fabric 402 with a first edge 402a and a second edge 402b. The piece of fabric 402 may be folded to form a cavity 404. The cavity 404 may be filled with batting. The first edge 402a and the second edge 402b may be folded inwards towards the cavity 404. The stitching 304 may be disposed within the cavity to render the stitching invisible from outside the fabric strip 400. Accordingly, the first edge 402a and the second edge 402b may be joined by an invisible seam stitch. The fabric strip 400 may form the first side strip 102, the top strip 104, the second side strip 106, the bottom strip 108, the first center strip 110, and/or the second center strip 112.

In an embodiment, the fabric strip 400 may be infused with a scent. For example, an essential oil may be deposited on and/or absorbed into a surface of the fabric strip 400. The essential oil may be absorbed into the piece of fabric 402 or may be absorbed into the batting inside the cavity 404. The piece of fabric 402 and/or the may be otherwise infused with the essential oil. In another example, a scent node may be disposed within the cavity 404. The scent node may include a body formed of a waxy and/or petroleum-based material and infused with a fragrance. The waxy and/or petroleum-based material may be selected based on how well it holds the fragrance. The scent node may release the fragrance as the scent node warms. Accordingly, as a user manipulates the sensory stimulation toy, the scent node may warm and release more fragrance than when the scent node was cooler. The scent may thereby enhance a therapeutic effect of use of the sensory stimulation toy for therapy.

Figure 5A:
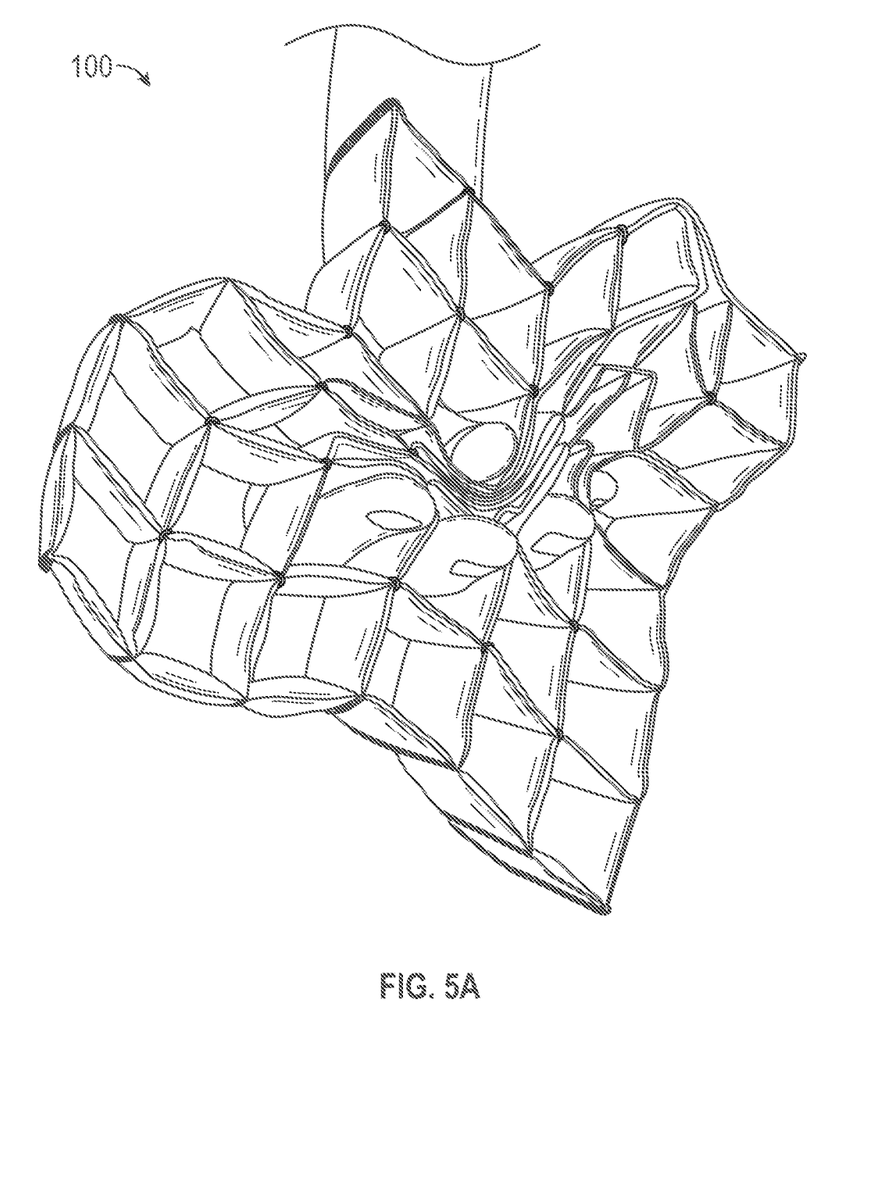
FIG. 5A illustrates a user manipulating a shape of a sensory stimulation toy with the fingers of the user into a first shape, according to an embodiment.

FIG. 5A illustrates a user manipulating a shape of the sensory stimulation toy 100 with the fingers of the user into a first shape, according to an embodiment. Some of the features in FIG. 5A are the same as or similar to some of the features in FIGS. 1-4 as noted by same and/or similar reference characters, unless expressly described otherwise. In one embodiment, the sensory stimulation toy 100 may be a plush toy that is flexible or bendable to be configured into different shapes. For example, the user may insert one or more of his/her fingers into the holes of the sensory stimulation toy 100. As the plush toy is flexible or bendable, the user may manipulate the shape of the sensory stimulation toy 100 by changing the positions of the user's fingers. As the user changes the position of his/her fingers, the shape of the sensory stimulation toy 100 may change.

In an embodiment, the sensory stimulation toy 100 may be made of a material that has a pliability and/or a compressibility to allow the sensory stimulation toy 100 to be collapsed and/or deformed by the hand of the user. The material may have a springiness sufficient to expand the sensory stimulation toy 100 after a force by the fingers or the hand that deforms or compresses the sensory stimulation toy 100 is removed. The sensory stimulation toy 100 may return to a restored shape similar to an original shape of the sensory stimulation toy 100 before the sensory stimulation toy 100 was deformed or compressed. The restored shape may be similar to, but still distinguishable from, the original shape. For example, in the original shape, the holes 114 of the sensory stimulation toy 100 may be open. In a compressed and/or deformed shape, the holes 114 may be closed. In the restored shape, the holes 114 may be open again, although not in an exactly same shape as the original shape. Despite this, in some embodiments, the restored shape may be exactly the same as the original shape.

In various embodiments, the sensory stimulation toy 100 may be used by a person receiving therapy, such as for a motor disability or a mental disability. In one example, as the user manipulates the shape of the sensory stimulation toy 100, the different shapes and the different color patterns of the sensory stimulation toy 100 (when the sensory stimulation toy 100 has different colored strips as discussed above) may help the user develop fine motor skills, hand-eye coordination, stress and anxiety relief, fine motor skills, and/or provide entertainment. In another example, when the user has difficulty processing sensory information, the different shapes and color patterns of the sensory stimulation toy 100 may help the user to focus or process information by stimulating one or more senses of the user. In another embodiment, the sensory stimulation toy 100 may be used to aid an individual undergoing hand function rehabilitation. For example, if an individual undergoes invasive hand surgery, the individual may need to participate in rehabilitation therapy to regain partial or full use of their hand. The individual may manipulate the shape of the sensory stimulation toy 100 as part of exercises and/or activities for regaining the use of their hand.

Figure 5B:
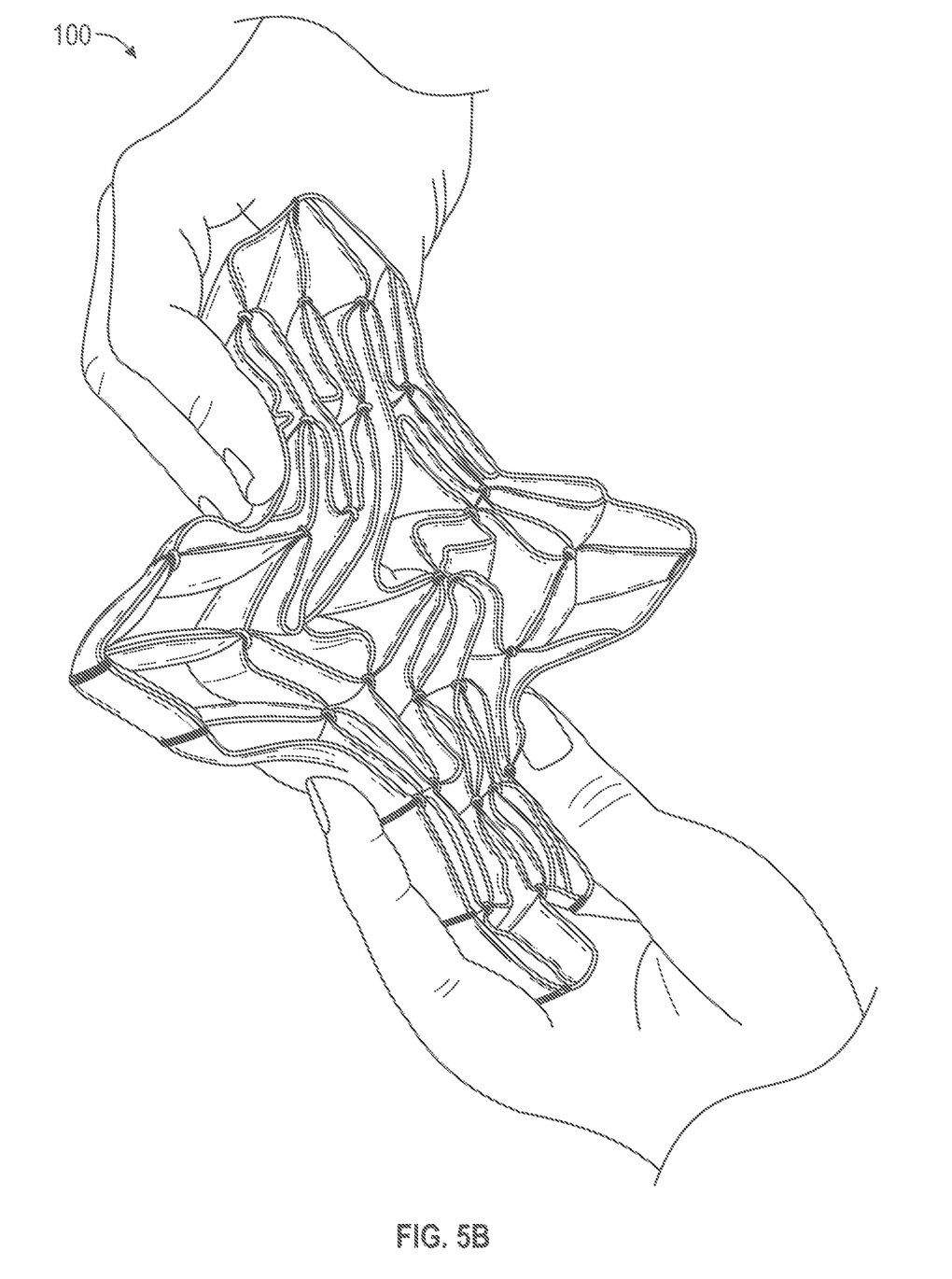
FIG. 5B illustrates a user closing hands around the sensory stimulation toy 100, according to an embodiment.

FIG. 5B illustrates a user closing hands around the sensory stimulation toy 100, according to an embodiment. Some of the features in FIG. 5B are the same as or similar to some of the features in FIGS. 1-5A as noted by same and/or similar reference characters, unless expressly described otherwise. Using the sensory stimulation toy 100 may include manipulation of the sensory stimulation toy 100 while the user's fingers are outside the holes. For example, the user may collapse the sensory stimulation toy 100 by pressing and/or closing the user's hands against the perimeter of the grid. The user may deform the grid in a direction parallel to a direction of the holes. The user may toss the sensory stimulation toy 100.

Figure 6:
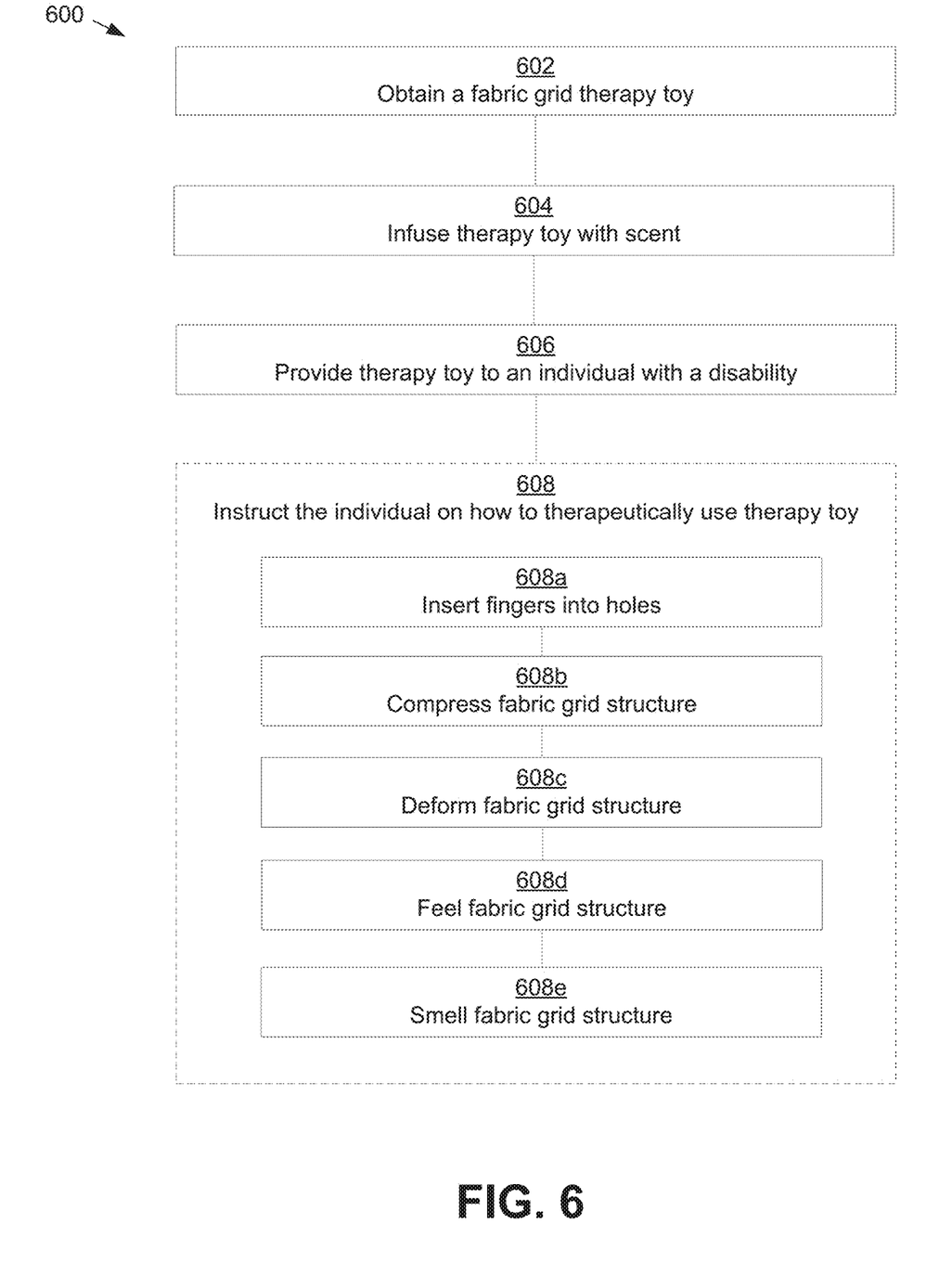
FIG. 6 illustrates a method 600 of using the sensory stimulation toy 100 for therapy, according to an embodiment.

FIG. 6 illustrates a method 600 of using the sensory stimulation toy 100 for therapy, according to an embodiment. Some of the features in FIG. 6 are the same as or similar to some of the features in FIGS. 1-5B as noted by same and/or similar reference characters, unless expressly described otherwise. The method 600 may include obtaining a fabric grid therapy toy such as the sensory stimulation toy 100 (block 602). The method 600 may include infusing the therapy toy with a scent (block 604). The scent may be sprayed onto the fabric grid therapy toy. The scent may be dripped onto the fabric grid therapy toy. The scent may be rubbed onto the fabric grid therapy toy. The scent may be infused into and/or otherwise integrated with the fabric grid therapy toy during manufacture of the fabric grid therapy toy. For example, a scent node may be disposed within a cavity of a strip of fabric forming a portion of the fabric grid therapy toy.

The method 600 may include providing the fabric grid therapy toy to an individual with a disability (block 606). The method 600 may include providing instructions to the individual on how to therapeutically use the fabric grid therapy toy (block 608). The instructions may include inserting a finger into one of a plurality of holes in the fabric grid structure (block 608a). the instructions may include compressing the fabric grid structure (block 608b). Compressing the fabric grid structure may be done by the user closing one or both hands around a perimeter structure of the fabric grid structure. The instructions may include deforming the fabric grid structure (block 608c). Deforming the fabric grid structure may include spreading and/or closing fingers as the fingers are inserted into the holes. The instructions may include felling the fabric grid structure (block 608d). Feeling the fabric grid structure may include sliding and/or dragging skin of the user across and/or against the fabric grid structure. For example, the user may slide the user's fingers through the holes and/or along the perimeter structure. The instructions may include smelling the fabric grid structure (block 608e). Smelling the fabric grid structure may expose the user to the scent infused into the fabric grid structure.

The user may be instructed to bring the fabric grid structure near a nose of the user and/or to breathe through the nose as the user manipulates the fabric grid structure. The fabric grid structure may release more fragrance as the user manipulates the fabric grid structure more, and the fabric grid structure may release less fragrance as the user manipulates the fabric grid structure less.

The disclosure above encompasses multiple distinct embodiments with independent utility. While these embodiments have been disclosed in a particular form, the specific embodiments disclosed and illustrated above are not to be considered in a limiting sense as numerous variations are possible. The subject matter of the embodiments includes the novel and non-obvious combinations and sub-combinations of the various elements, features, functions and/or properties disclosed above and inherent to those skilled in the art pertaining to such embodiments. Where the disclosure or subsequently filed claims recite "a" element, "a first" element, or any such equivalent term, the disclosure or claims is to be understood to incorporate one or more such elements, neither requiring nor excluding two or more such elements.

Applicant(s) reserves the right to submit claims directed to combinations and sub-combinations of the disclosed embodiments that are believed to be novel and non-obvious. Embodiments embodied in other combinations and sub-combinations of features, functions, elements and/or properties may be claimed through amendment of those claims or presentation of new claims in the present application or in a related application. Such amended or new claims, whether they are directed to the same embodiment or a different embodiment and whether they are different, broader, narrower or equal in scope to the original claims, are to be considered within the subject matter of the embodiments described herein.

The invention claimed is:

1. An apparatus, comprising:
a fabric grid structure comprising:
a perimeter sub-structure comprising:
a first side strip;
a top strip;
a second side strip;
a bottom strip, wherein:
a first end of the first side strip is attached to a first end of the top strip;
a second end of the top strip is attached to a first end of the second side strip;
a second end of the second side strip is attached to a first end of the bottom strip; and
a second end of the bottom strip is attached to a second end of the first side strip; and
a center grid sub-structure comprising:
a first center strip; and
a second center strip, wherein:
the first center strip extends diagonally across the fabric grid structure from the first side strip to the bottom strip;
the second center strip extends diagonally across the fabric grid structure from the top strip to the second side strip;
the first center strip and the second center strip are connected at a first set of multiple points, wherein the first set of multiple points are positioned along the first center strip and the second center strip to form a plurality of holes within the center grid sub-structure configured to receive one or more fingers in the plurality of holes to manipulate a shape of the fabric grid structure; and
wherein:
the fabric grid structure is configured in shape, size, texture, or scent to stimulate a first sense or a second sense of a person as the person manipulates the fabric grid structure;
the first sense is different from the second sense; and
the fabric grid structure comprises a material having a pliability or a compressibility sufficient to allow the fabric grid structure to be collapsed or deformed by a hand of the person.

2. The apparatus of claim 1, wherein the fabric grid structure is collapsed or deformed as:
fingers of the person are inserted in the holes; or
as the hand closes around the first side strip, the top strip, the second side strip, or the bottom strip.

3. The apparatus of claim 1, wherein:
the material has a springiness sufficient to expand the fabric grid structure after a force by the fingers or the hand that deforms or compresses the fabric grid structure is removed; and
the fabric grid structure returns to a restored shape similar to an original shape of the fabric grid structure before the fabric grid structure was deformed or compressed.

4. The apparatus of claim 1, wherein the fabric grid structure further comprises corner stitching that forms a corner of the fabric grid structure, wherein the corner stitching:
attaches the first end of the first side strip to the first end of the top strip;
attaches the second end of the top strip to the first end of the second side strip;
attaches the second end of the second side strip to the first end of the bottom strip; or
attaches the second end of the bottom strip to the second end of the first side strip.

5. The apparatus of claim 1, further comprising a scent infused into the fabric grid structure, wherein:
the first sense comprises smell;
the scent is infused as:
an essential oil absorbed into a surface of the first side strip, the top strip, the second side strip, the bottom strip, the first center strip, or the second center strip; or
a scent node disposed within the first side strip, the top strip, the second side strip, the bottom strip, the first center strip, or the second center strip; and
the scent enhances a therapeutic effect of use of the fabric grid structure for therapy by stimulating the first sense.

6. The apparatus of claim 1, further comprising:
a first attachment point where the first side strip and the top strip attach to each other;
a second attachment point where the first center strip and the first side strip attach to each other; and
a third attachment point where the first center strip attaches to the second center strip, wherein:
a width of a first segment between the first attachment point and the second attachment point is approximately equal to a length of a second segment between the second attachment point and the third attachment point;
the first segment is adjacent to the second segment; and
the first segment is perpendicular to the second segment.

7. The apparatus of claim 1, further comprising:
a third center strip that extends diagonally across the fabric grid structure from the first side strip to the bottom strip;
a fourth center strip that extends diagonally across the fabric grid structure from the top strip to the second side strip;
wherein:
    the third center strip and the first center strip are connected at a second set of multiple points;
    the second set of multiple points is positioned along the third center strip and the first center strip;
    points of the second set of multiple points alternate with points of the first set of multiple points;
    the fourth center strip and the second center strip are connected at a third set of multiple points;
    the third set of multiple points is positioned along the fourth center strip and the second center strip;
    points of the third set of multiple points alternate with the points of the first set of multiple points;
    the third center strip pulls the first center strip away from the second center strip; and
    the fourth center strip pulls the second center strip away from the first center strip.

8. The apparatus of claim 7, wherein:
the first center strip comprises a first color pattern;
the second center strip comprises a second color pattern;
the third center strip comprises a third color pattern; and
the fourth center strip comprises a fourth color pattern.

9. The apparatus of claim 1, wherein:
the first center strip comprises a first fabric; and
the second center strip comprises a second fabric, wherein:
    the second sense comprises a touch sense; and
    the second fabric comprises a different texture than the first fabric to stimulate the second sense.

10. The apparatus of claim 1, wherein:
the first side strip, the top strip, the second side strip, the bottom strip, the first center strip, or the second center strip is filled with batting;
the first side strip, the top strip, the second side strip, the bottom strip, the first center strip, or the second center strip comprises a piece of fabric folded around the batting; and
the piece of fabric is stitched around the batting with an invisible seam stitch.

* * * * *